(12) United States Patent
Bae et al.

(10) Patent No.: US 8,618,357 B2
(45) Date of Patent: Dec. 31, 2013

(54) **SWEETPOTATO *SRD1* CDNA AND TRANSGENIC PLANTS WITH HIGH-NUMBERED STORAGE ROOTS USING THE SAME**

(75) Inventors: Jung Myung Bae, Seoul (KR); Jeong Sheop Shin, Seoul (KR); Seol Ah Noh, Seoul (KR); Kyung Hee Paek, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 433 days.

(21) Appl. No.: 12/896,554

(22) Filed: Oct. 1, 2010

(65) Prior Publication Data
US 2011/0239328 A1 Sep. 29, 2011

(30) Foreign Application Priority Data
Mar. 29, 2010 (KR) .................. 10-2010-0028208

(51) Int. Cl.
| | | |
|---|---|---|
| *C07K 14/415* | (2006.01) |
| *C12N 15/82* | (2006.01) |
| *A01H 5/00* | (2006.01) |
| *A01H 1/00* | (2006.01) |

(52) U.S. Cl.
USPC ........ 800/298; 800/278; 800/290; 435/320.1; 435/252.3; 530/370

(58) Field of Classification Search
None
See application file for complete search history.

(56) References Cited

U.S. PATENT DOCUMENTS

2008/0155706 A1* 6/2008 Riechmann et al. .......... 800/260

OTHER PUBLICATIONS

Bowie et al, Science 247:1306-1310, 1990.*
McConnell et al, Nature 411 (6838):709-713, 2001.*
Haung et al (2001, NCBI Accession No. AF396746).*
Noh et al., "SRD1 Is Involved in the Auxin-Mediated Initial Thickening Growth of Storage Root in Sweetpotato", RNA Biology and Diseases: The 21st Annual Meeting of the Korean Society for Molecular and Cellular Biology, 2009, E-13, p. 215.
Noh et al., "SRD1 Is Involved in the Auxin-Mediated Initial Thickening Growth of Storage Root in Sweetpotato", Plant & Animal Genomes XVIII Conference, Jan. 9-13, 2010, San Diego, CA.
Noh, et al., "SRD1 Is Involved in the Auxin-Mediated Initial Thickening Growth of Storage Root by Enhancing Proliferation of Metaxylem and Cambium Cells in Sweetpotato (*Ipomoea batatas*)", Journal of Experimental Botany Advance Access, Feb. 11, 2010, pp. 1-13.

* cited by examiner

*Primary Examiner* — Stuart F Baum
(74) *Attorney, Agent, or Firm* — Edwards Wildman Palmer LLP

(57) ABSTRACT

Disclosed herein are a sweetpotato SRD1 cDNA, a plant transformation vector carrying the same, and a transgenic plant comprising the vector. The thickening growth of storage roots of the transgenic sweetpotato prepared using the SRD1 cDNA is stimulated, increasing the number of storage roots by up to two times. Therefore, SRD1 according to the present subject matter is useful in the generation of transgenic root crops with high-numbered storage roots or early-maturing storage root plants.

14 Claims, 13 Drawing Sheets
(9 of 13 Drawing Sheet(s) Filed in Color)

```
              *        20         *        40         *        60
SRD1    : MGRGKVEIRRIEKSTNRRVTFWKRRNGLFKKAMEMGILCDAEVGLMIFSSTGKLHEFATT :  60
IbMADS1 : MGRGKVEIRRIEKSTNRRVTFWKRRNGLLKKAMEMGILCDAEVGLMIFSSTGKLHEFATT :  60

*        80         *       100         *       120
SRD1    : SIRSVIERYNKTQGDSLQSPLDPTLELKFWQIEVAILRQQLHRMQEDHRKVMGEVYGLSV : 120
IbMADS1 : SIRSVIERYNKTQGDSLQSPLDPTLELKFWQIEVAILRQQLHRMQEDHRKVMGEVYGLSV : 120

*       140         *       160         *       180
SRD1    : KDLQNLENQLEMSLSGIRMKKEQILIEQIQELTHK-GSFVHQENFELFNKFQAYGTSDPN : 179
IbMADS1 : KDLQNLENQLEMSLSGIRMKKEQILIEQIQELTHKQGSFVHQENFELFNKFQAYGTSDPN : 180

*       200         *
SRD1    : AVNGDTISPYDFTISEESQGHTHFQLPQNFSDLARALY : 217   (SEQ ID NO.: 2)
IbMADS1 : AVNGDTISPYDFTISEESQGHTHFQLPQNFSDLARALY : 218   (SEQ ID NO.: 5)
```

FIG. 3

```
                          198              558 559
                           |                |   |
    SRD1      ------GTTTAAGAA-----------CAAG---GGGA----  (SEQ ID NO.:16)
    BU690229  ------GTTTAAGAA-----------CAAG---GGGA----  (SEQ ID NO.:16)
    BU690638  ------GTTTAAGAA-----------CAAG---GGGA----  (SEQ ID NO.:16)
    BU690685  ------GTTTAAGAA-----------CAAG---GGGA----  (SEQ ID NO.:16)
    BU690779  ------GTTTAAGAA-----------CAAG---GGGA----  (SEQ ID NO.:16)
    BU690909  ------GTTTAAGAA-----------CAAG---GGGA----  (SEQ ID NO.:16)
    BU691031  ------GTTTAAGAA-----------CAAG---GGGA----  (SEQ ID NO.:16)
    BU691319  ------GTTTAAGAA-----------CAAG---GGGA----  (SEQ ID NO.:16)
    BU691378  ------GTTTAAGAA-----------CAAG---GGGA----  (SEQ ID NO.:16)
    BU691821  ------GTTTAAGAA-----------CAAG---GGGA----  (SEQ ID NO.:16)
    IbMADS1   ------GTTGAAGAA-----------CAAGCAGGGGA----  (SEQ ID NO.:17)
    BU691070  ------GTTGAAGAA-----------CAAGCAGGGGA----  (SEQ ID NO.:17)
    BU691835  ------GTTGAAGAA-----------CAAGCAGGGGA----  (SEQ ID NO.:17)
```

FIG. 12
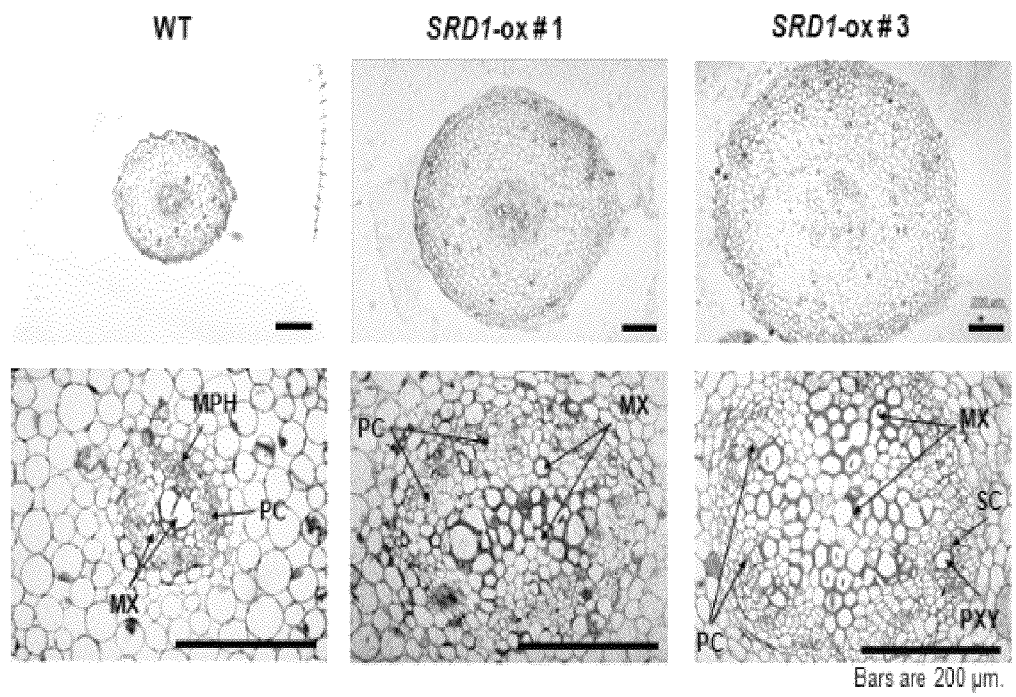
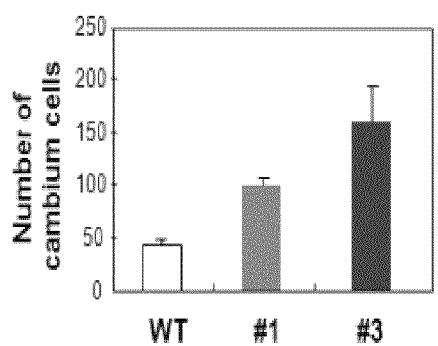
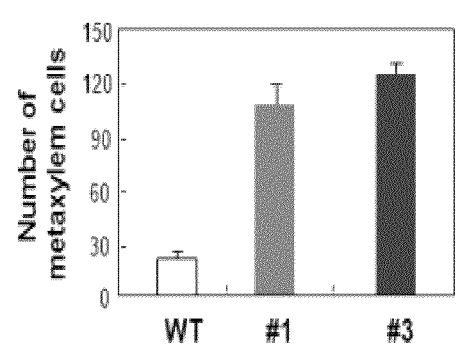

SWEETPOTATO *SRD1* CDNA AND TRANSGENIC PLANTS WITH HIGH-NUMBERED STORAGE ROOTS USING THE SAME

RELATED PATENT APPLICATION

This application claims the benefit of Korean Patent Application No. 10-2010-0028208, filed on Mar. 29, 2010, in the Korean Intellectual Property Office, the disclosure of which is incorporated herein in its entirety by reference.

REFERENCE FOR SEQUENCE LISTING SUBMITTED ELECTRONICALLY

The official copy of the sequence listing is submitted electronically via EFS-Web as an ASCII formatted sequence listing with a file name "31062U_Sequence_Listing.txt", created on Oct. 1, 2010, and having a size of 9.93 kilobytes and is filed concurrently with the specification. The sequence listing contained in this ASCII formatted document is part of the specification and is herein incorporated by reference in its entirety.

FIELD OF THE INVENTION

The present subject matter relates to a sweetpotato SRD1 cDNA for transgenic root crops with high-numbered storage roots using the same. More particularly, the present subject matter relates to a sweetpotato SRD1 cDNA, a transformation vector carrying the same, and a method of preparing a transgenic root crop with high-numbered storage roots that has an increased number of storage roots.

BACKGROUND OF THE INVENTION

Sweetpotato is the world's seventh most important food crop, and its storage roots provide high levels of digestible nutrients and it has a high plant biomass per hectare. In the early stages of the development of its roots, it forms colorless fibrous roots. As root development proceeds, some of these fibrous roots become pigmented and begin to swell, ultimately developing into storage roots.

Based on early anatomical studies on storage root morphogenesis (Kokubu, 1973, Bulletin of the Faculty of Agriculture, Kagoshima University 23, 1-126; Wilson and Lowe, 1973, Annuls in Botany 37, 633-643; Nakatani and Komeichi, 1991), a storage root has been defined as a root in which there is anomalous secondary cambial activity inside of a primary cambium. Both the linear growth and the promotion of the thickening growth of the storage root and/or the yield of storage roots have been shown to be affected by environmental factors, including soil temperature, humidity, light, photoperiod, carbon dioxide, and drought (Loretan et al., 1994, Advances in Space Research 14, 277-280; Hill et al., 1996, Acta Horticulturae 440, 25-30; Mortley et al., 1996, Acta Horticulturae 440, 31-36; Eguchi et al., 1998, Biotronics 27, 93-96; Pardales et al., 1999, Plant Production Science 2, 247-251; Kano and Ming, 2000, Environment Control in Biology 38, 113-120; van Heerden and Laurie, 2008, Physiologia Plantarum 134, 99-109).

As mentioned above, some of the fibrous roots ultimately develop into storage roots. Particularly, it is reported that the number of storage roots decreases at a soil temperature of 40° C. compared to at 25° C., whereas the number of storage roots increases at a soil temperature of 20-36° C. compared to at 13-31° C. (Pardales et al., 1999, Plant Prod. Sci. 2, 247-251).

To date, however, the molecular mechanism related to the development from fibrous roots to storage roots has not been reported. Regulating the development process from fibrous roots to storage roots will enable the production of sweetpotato to be increased.

Improvements in various molecular approaches have enabled the mining of genes involved in storage root development in the sweetpotato, resulting in the identification of a number of genes that are differentially expressed in developing storage roots (You et al., 2003, FEBS Letters 536, 101-105; Tanaka et al., 2005, Journal of Plant Physiology 162, 91-102). Based on the results of their comparison of the distribution of KNOX1 gene expression and endogenous trans-zeatin riboside (t-ZR) in sweetpotato roots, Tanaka et al. (2008) suggested three sweetpotato class 1 knotted1-like homeobox (KNOX1) genes as possible regulators of cytokinin levels in storage roots (Tanaka et al., 2008, Journal of Plant Physiology 165, 1726-1735).

Ku et al. (2008, Annals of Botany 102, 57-67) recently isolated IbMADS1 from sweetpotato and analyzed its functional role in storage root development using potato overexpressing IbMADS1. However, to date, due to the difficulty of generating transgenic sweetpotato plants, researchers have been unable to verify directly whether a sweetpotato gene is actually involved or not, in the formation or thickening growth of storage roots using sweetpotato gain and/or loss of function mutants.

Meanwhile, most high value-added storage root plants, such as ginseng, are cultivated for several years. During the growth period, storage roots are susceptible to infection by various pathogen fungi, resulting in rot in their roots before harvest time.

Particularly, it is now reported that the portion of uprooting due to root rotting is up to approximately 50% in the field for the six-year old ginseng that is representative of high value-added storage root plants in Korea. To minimize such damage to the cultivation of storage root plants, generation of a cultivar resistant to root rot is required, along with development of a cultivation method that shortens the cultivation period. Identification of the genes involved in the development of storage roots and functional characterization of the genes are prerequisites for the molecular breeding.

Therefore, in order to increase storage root production, there has been a need to develop transgenic root plants bearing high-numbered storage roots or early-maturing transgenic root plants using genes involved in the storage root development.

SUMMARY OF INVENTION

Accordingly, the present subject matter has been made keeping in mind the above problems and needs occurring in the prior art, and an object of the present subject matter is to provide sweetpotato SRD1 cDNA with which transgenic root crops with high-numbered storage roots can be prepared.

It is another object of the present subject matter to provide a plant transformation vector carrying SRD1 cDNA. It is a further object of the present subject matter to provide a transgenic root crop with high-numbered storage roots that comprises a vector carrying the SRD1 cDNA. The other objects and advantages of the present subject matter will be more clearly understood from the detailed description, claims and drawings, of the present application.

In accordance with an aspect of the present subject matter, there is provided an isolated DNA molecule, comprising a nucleotide sequence of SEQ ID NO.: 1.

Preferably, the isolated DNA molecule is a cDNA synthesized from a sweetpotato SRD1 gene.

In accordance with another aspect of the present subject matter, there is provided an isolated DNA molecule, comprising a nucleotide sequence encoding a polypeptide comprising an amino acid sequence of SEQ ID NO.: 2.

Also provided is a binary vector for transforming plants, comprising the DNA molecule, in accordance with a further aspect of the present subject matter.

In still another aspect, the present subject matter provides a microorganism, comprising the DNA molecule or the vector.

In still a further aspect, the present subject matter provides a transgenic plant, comprising the DNA molecule or the vector.

In yet another aspect, the present subject matter provides an open reading frame (ORF) of the sweetpotato SRD1 gene, comprising a nucleotide sequence of SEQ ID NO.: 3.

In yet a further aspect, the present subject matter provides a binary vector for transforming plants comprising the ORF of the sweetpotato SRD1 gene.

In yet still a further aspect, the present subject matter provides a microorganism, comprising the ORF or the vector.

In yet still a further aspect, the present subject matter provides a transgenic plant, comprising the ORF or the vector.

In yet still a further aspect, the present subject matter provides an isolated polypeptide, translated from the ORF, comprising an amino acid sequence of SEQ ID NO.: 2.

In yet still a further aspect, the present subject matter provides a method for increasing the number of plant storage roots, comprising introducing the binary vector into plants.

In yet still a further aspect, the present subject matter provides a method for stimulating the thickening growth of plant storage roots, comprising introducing the binary vector into plants.

In still yet another aspect, the present subject matter provides a method for producing the homogenous-sized storage roots of a plant, comprising introducing the binary vector into the plant.

In a final aspect, the present subject matter provides a method for regulating the development stage of a plant storage root, comprising inducing the expression of SRD1 by treating the storage root plants with auxin.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and advantages of the present subject matter will be more clearly understood from the following detailed description taken in conjunction with the accompanying drawings, in which:

FIG. 1 shows a comparison of the nucleotide sequence of the sweetpotato SRD1 cDNA of the present subject matter, with the nucleotide sequence of IbMADS1 cDNA. The blue arrows indicate the location of SRD1-specific primers.

FIG. 2 shows a comparison of the amino acid sequence encoded by of the sweetpotato SRD1 cDNA of the present subject matter with the amino acid sequence encoded by IbMADS1 cDNA.

FIG. 3 shows a comparison of the nucleotide sequence of the sweetpotato SRD1 and IbMADS1 with the nucleotide sequences of MADS-box cDNAs isolated from early-stage storage roots of sweetpotato (*Ipomoea batatas* cv. "Jinhongmi"). The numbers above the nucleotide sequences indicate the number of the nucleotide in the sequence of SRD1 cDNA.

FIG. 12 shows a comparison of the cell differentiation of roots in the SRD1-ox sweetpotato plants in which sweetpotato SRD1 cDNA of the present subject matter has been inserted, with the cell differentiation of wild type roots.

DETAILED DESCRIPTION OF THE INVENTION

Figure 4:
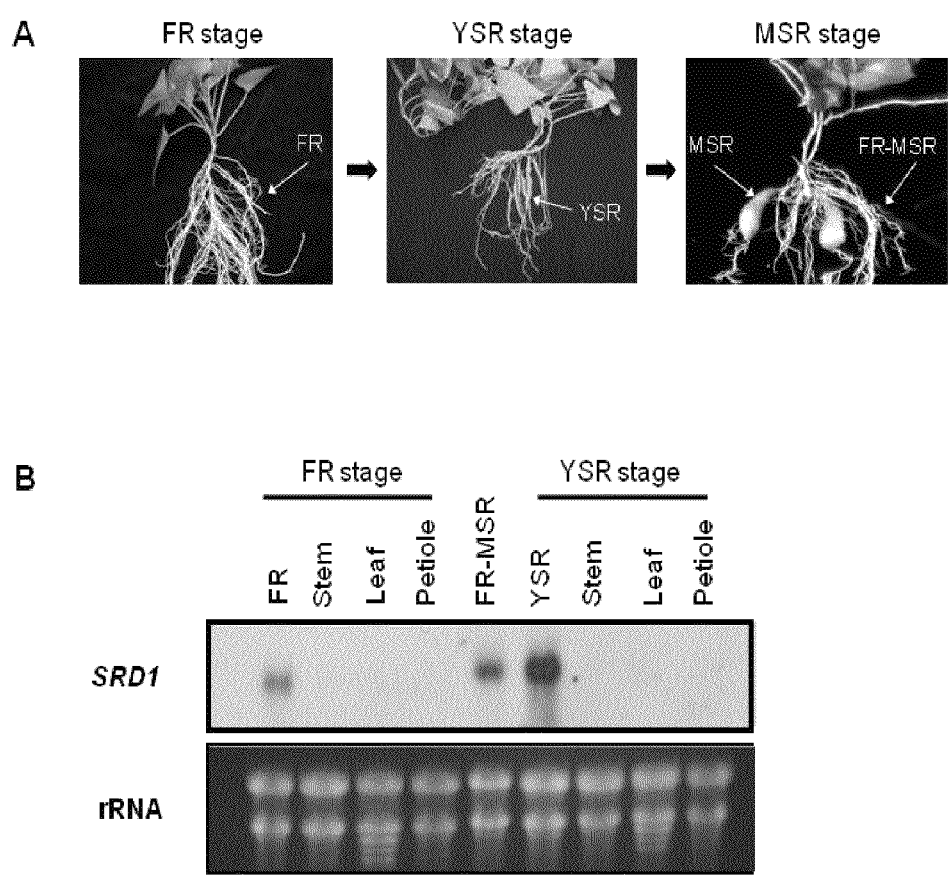
FIG. 4 shows the expression pattern of sweetpotato SRD1 of the present subject matter. (A), developmental stages of sweetpotato, (B) RNA gel blot analysis of SRD1 in the sweetpotato. FR, fibrous root; YSR, young storage root; MSR, mature storage root; FR-MSR, fibrous root from mature storage root stage.

In order to accomplish the objects, the present inventors have succeeded in cloning a sweetpotato SRD1 cDNA, constructing a binary vector, suitable for plant transformation, carrying the clone, and transforming the vector into sweetpotato. The transgenic sweetpotato was found to produce significantly increased numbers of storage roots, and, notably, two times as many storage roots.

In one aspect, therefore, the present subject matter provides an isolated DNA molecule, comprising a nucleotide sequence of SEQ ID NO.: 1.

Preferably, the isolated DNA molecule is a cDNA synthesized from a sweetpotato SRD1 gene.

The cDNA has a nucleotide sequence 1,002 bp long, consisting of 93 bp 5'-UTR, a 654 bp ORF (open reading frame; SEQ ID NO.: 3; coding 217 amino acid), and a 255 bp 3'-UTR.

In accordance with another aspect, the present subject matter provides an isolated DNA molecule, comprising a nucleotide sequence encoding a polypeptide comprising an amino acid sequence of SEQ ID NO.: 2.

In accordance with a further aspect, the present subject matter provides a binary vector for transforming plants, the vector carrying the sweetpotato SRD1 cDNA.

The plant transformation vector is a binary vector capable of stably expressing an exogenous gene of interest in the plants.

In a pMBP1 vector, the sweetpotato SRD1 cDNA of the present subject matter is located between a CaMV35S promoter and an NOS terminator. It should be understood by those skilled in the art that any other plant transformation vector may be used instead of the pMBP1 vector.

In accordance with a further aspect, the present subject matter provides transgenic sweetpotato carrying the sweetpotato SRD1 cDNA of the present subject matter in a binary vector.

The binary vector may be introduced into plants using *Agrobacterium* or a gene gun. In an embodiment of the present subject matter, an *Agrobacterium* method was used for transforming sweetpotatoes.

In addition to sweetpotato, the sweetpotato SRD1 cDNA of the present subject matter may be introduced into any plant that is adapted to have the thickening growth of its storage roots increased or the number of storage roots increased. Preferably, plants are high value-added storage root plants such as sweetpotato and ginseng.

In accordance with still another aspect, the present subject matter provides an isolated polypeptide, translated from the ORF of the sweetpotato SRD1 gene, comprising an amino acid sequence of SEQ ID NO.: 2.

Further, the present subject matter provides a method for increasing the number of plant storage roots, comprising introducing the sweetpotato SRD1 cDNA of the present subject matter into plants. In accordance with the present subject matter, it will be possible to increase total production of storage roots by generating plants with high-numbered storage roots.

In yet still a further aspect, the present subject matter provides a method for stimulating the thickening growth of plant storage roots, comprising introducing the sweetpotato SRD1 cDNA of the present subject matter into plants. In accordance with the aspect of the present subject matter, growing period of the high value-added plants like ginseng can be reduced, resulting in less damage from root diseases and improved productivity of root crops which contributes to increasing a farmer's income.

In still yet another aspect, the present subject matter provides a method for producing the homogenous-sized storage roots of a plant, comprising introducing the sweetpotato SRD1 cDNA of the present subject matter into the plant. In accordance with the aspect of the present subject matter, it will be possible to improve the quality of storage root crops.

In a final aspect, the present subject matter provides a method for regulating the development stage of a plant storage root, comprising inducing expression of the SRD1 by treating the storage root plants with auxin. Expression of the SRD1 of the present subject matter is increased by treatment with exogenous auxin and overexpression of the SRD1 improves the productivity of storage roots. Preferably, such treatment is performed during a prescribed period at a specific concentration. For instance, it is preferable to treat the plants with 500-2000 μM of auxin. It is also preferable to treat for 6-12 hours with 500 μM of auxin.

A better understanding of the present subject matter may be obtained through the following examples, which are set forth to illustrate, but are not to be construed as the limit of the present subject matter.

EXAMPLE 1

Sequence Analysis of Sweetpotato SRD1 cDNA

Total RNA was isolated from an early-stage storage root of sweetpotato and was used to construct an EST (Expressed Sequence Tag) library. Using this library, 2,859 ESTs were cloned and deposited in the National Center for Biotechnology Information (NCBI) with NCBI Accession Nos.: BU690119-BU692977 (You et al., 2003, FEBS Letters 536, 101-105). Of them, the cDNA of a MADS-box protein was identified and sequencing analysis revealed that the cDNA clone was 1,002 bp long comprising of 93 bp of 5' untranslated region (UTR), 654 bp of ORF (Open Reading Frame, 217 amino acid) and 255 bp 3' UTR. This clone was registered under the name of 'a sweetpotato MADS-box cDNA' in NCBI (NCBI accession no. FJ237529) and subsequently designated SRD1 (Storage Root Development-related gene 1).

Figure 1:
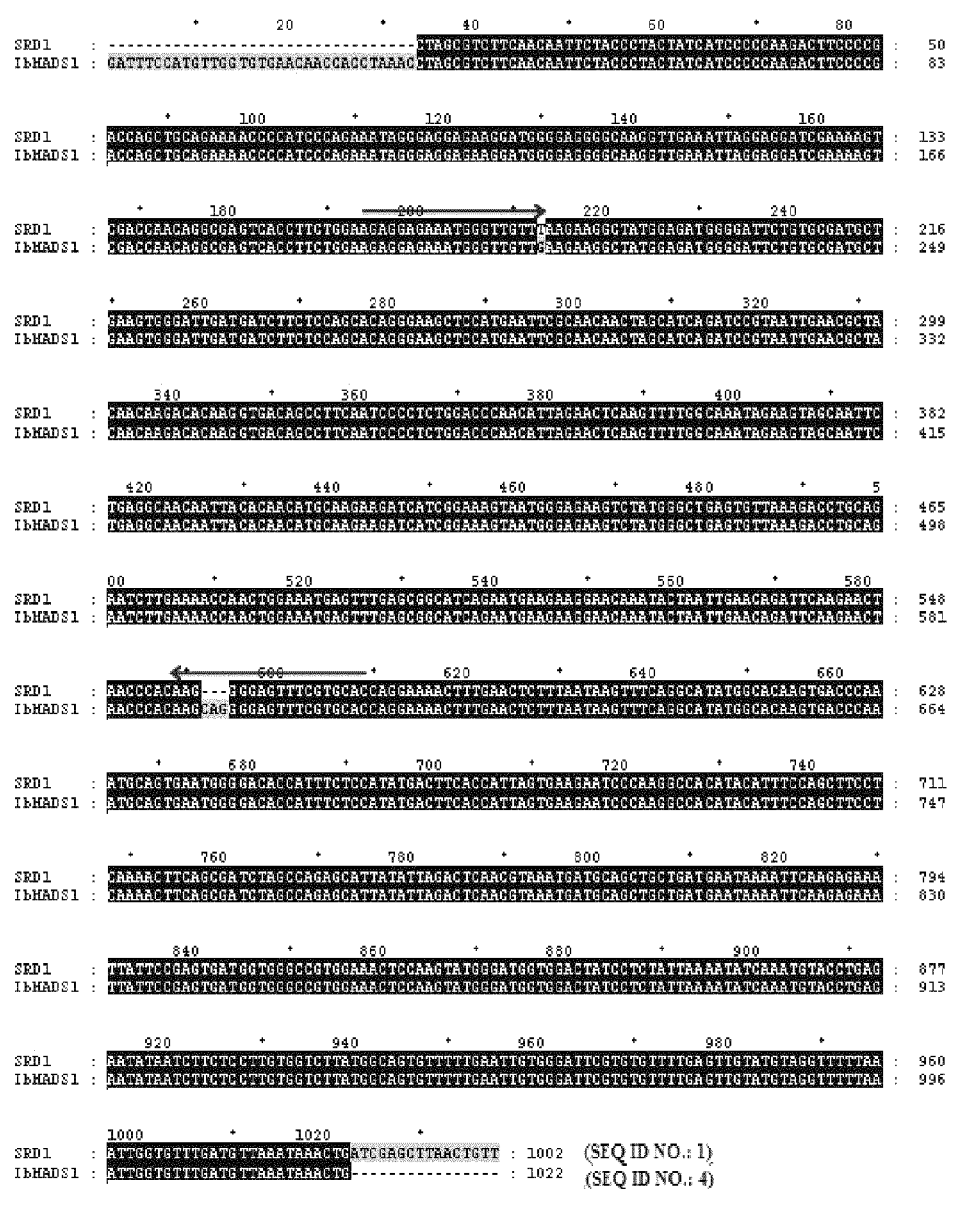

The nucleotide sequence of SRD1 was found to have 99% identity with the previously reported IbMADS1 cDNA in the overlapping region (Ku et al., 2008, Annals of Botany 102, 57-67) (FIG. 1). Compared with IbMADS1 cDNA (SEQ ID NO.: 4), the SRD1 cDNA is 33 bp shorter in the 5'-UTR and 30 bp longer in the 3' UTR, and contains a single nucleotide polymorphism (SNP) (thymine to guanine) at nucleotide 180 and a 3 bp deletion between nucleotides 558 and 559 in the open reading frame (ORF) region. This alteration in nucleotide sequence results in a single residue change (phenylalanine to leucine) at amino acid 29 in the IbMADS1 amino acid sequence (SEQ ID NO.: 5) and a single residue deletion (glutamine in IbMADS1) between amino acids 155 and 156 of SRD1 (FIG. 2).

To determine whether SRD1 is an allelic variant of IbMADS1 or a gene distinct from IbMADS1, the presence of the IbMADS1 gene in the genome of *I. batatas* cv. 'Jinhongmi' was investigated. Eleven MADS-box protein sequences were identified among the 2,859 ESTs isolated from the early-stage storage root cDNA library mentioned above (You et al., 2003, *FEBS Letters* 536, 101-105). Sequence comparison of these 11 MADS-box gene cDNAs revealed that nine and two cDNAs showed perfect sequence identity with the SRD1 sequence and IbMADS1 sequence, respectively (FIG. 3, SEQ ID NO.: 16-17). These results suggest that both the SRD1 and IbMADS1 genes are present as a distinct gene in the genome of *I. batatas* cv. 'Jinhongmi' and that both are expressed in the storage root. They also indicate that SRD1 is a major MADS-box protein gene in the early-stage storage root.

EXAMPLE 2

Expression Pattern Analysis of SRD1

(i) Method for Northern Blotting

Total RNA was extracted from various tissues, including the leaf, petiole, stem, fibrous root, and storage root tissues, at three different developmental stages [FR: fibrous root (diameter<0.2 cm), YSR: young storage root (diameter 0.5~1.0 cm), and MSR: mature storage root (diameter>5.0 cm)] (FIG. 4A) using a 4.4M guanidinium-SDS lysis buffer (Chirgwin et al., 1979 Biochemistry 18, 5294-5299) and 5.7M CsCl gradient (Glisin et al., 1974, Biochemistry 13, 2633-2637) as described in You et al. (2003, FEBS Letters 536, 101-105). Total RNA (25 μg) was denatured, electrophoresed in the 1% agarose-formaldehyde gel, and then transferred onto nylon membranes (Tropilon-Plus™; Tropix, USA) using the downward alkaline capillary method.

A probe was obtained by PCR amplification of a plasmid (2.5 ng) carrying a 1 kb SRD1 cDNA, which was performed in a PCR mixture containing 100 μM of dNTP exclusive of dCTP, 100 μM of dCTP-biotin, 10 μM of vector (pBluescript II) primers T3 (5'-AATTAACCCTCACTAAAGGG-3'; SEQ ID NO.: 6) and T7 (3'-CGGGATATCACTCAGCATAATG-5'; SEQ ID NO.: 7) each, 1×PCR buffer, and 1 unit of Taq polymerase to a final volume of 10 μl, starting with pre-denaturation at 95° C. for 5 min before 30 cycles of denaturation at 95° C. for 30 sec, annealing at 58° C. for 20 sec and extension at 72° C. for 30 sec.

The PCR-amplified biotinylated probe was purified using a QIAquick™ PCR purification kit (QIAGEN, Germany) and was added in an amount of about 100 ng onto the membrane, followed by hybridization at 65° C. or 68° C. for 18 hrs. The membrane was washed twice with 2×SSC/1% SDS at room temperature for 5 min, then twice with 0.1×SSC/1% SDS at room temperature for 15 min, and finally twice with 1×SSC at room temperature for 5 min. Probe detection was performed using a Southern-star™ kit (Tropix, USA). The blots were treated with a blocking buffer (1×PBS, 0.2% I-Block™ Reagent and 0.5% SDS) and labeled with alkaline phosphatase-conjugated streptavidin, followed by treatment with CDP-Star™ (Ready-to-Use). The membrane was exposed to an X-ray film (Fujifilm, Japan) for a period ranging from 10 min to 1.5 hrs.

(ii) Expression Pattern Analysis of SRD1

The biotinylated probe was obtained by amplification of a 1 kb SRD1 cDNA through PCR and was used for Northern blotting. The SRD1 transcript was detected only in the fibrous roots of plants that had no storage roots and no matured storage root, but not in stem, leaf, and petiole tissues at any developmental stage (FIG. 4B). The transcript level of SRD1 was low in fibrous roots from both the fibrous root and mature storage root stages, but it increased in young storage roots, indicating that the expression of SRD1 is root specific and increases during the early developmental stage of the storage root.

EXAMPLE 3

Subcellular Localization Analysis of SRD1

The SRD1 cDNA fused to green fluorescent protein (GFP) was introduced into onion cells in an attempt to determine the subcellular localization of SRD1. The coding sequence of SRD1 (651 bp) was amplified using primers SRD1-103 (5'-CATCCCGGGATGGGGAGGGGCAAG-3'; SEQ ID NO.: 8) and SRD1-920R (5'-GTGAGCTCCACTGCCATAA-GACCACAA-GG-3'; SEQ ID NO.: 9). The resulting PCR product was fused in-frame to the coding region of smGFP to generate the SRD1::smGFP fusion construct under the control of the cauliflower mosaic virus (CaMV) 35S promoter. A transient transformation was performed as described by Chiu et al. (1996, Current Biology 6, 325-330). Onion epidermal cell segments were peeled and placed on a ½ MS medium (Murashige and Skoog, 1962) plate [half-strength MS salts (Duchefa), 0.3% phytagel (Sigma)]. SRD1::smGFP plasmid DNA (1 μg) was introduced into onion epidermal segments using a biolistic gun device (PDS-1000/He; Bio-Rad) with the following parameters: the stopping screen was positioned 3 cm below the rupture disk; the target tissue was positioned 6 cm below the stopping screen; and, helium pressure was 1100 psi. After bombardment, the tissues were incubated for 24 h at room temperature (25° C., darkness). Green fluorescence was observed using a fluorescence microscope (Olympus, Japan).

Figure 5:
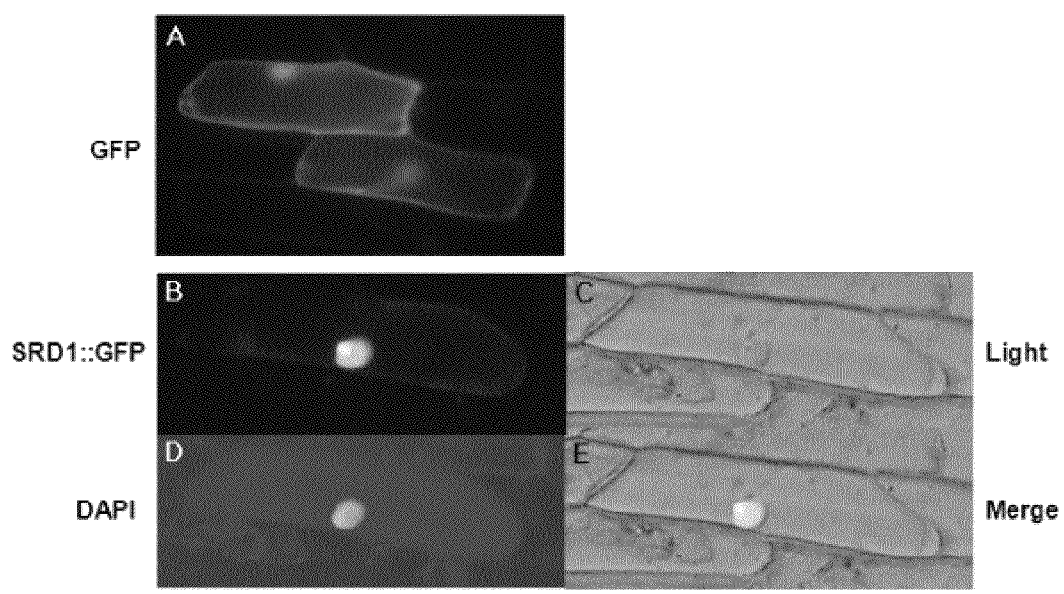
FIG. 5 shows subcellular localization of SRD1 protein expressed by sweetpotato SRD1 of the present subject matter. (A) The control GFP, (B-E) SRD1::GFP fusion protein, (A, B, D) Fluorescent images, (C, E) visible light images, (D) onion cells were stained with the DNA binding dye DAPI, (E) merged image of GFP with DAPI signal. GFP, green fluorescent protein; DAPI, 4#, 6-diamidino-2-phenylindole.

Onion cells transformed with the plasmid expressing only GFP showed a green fluorescence throughout the cell. In contrast, fluorescence was detected predominantly in the nucleus in cells transformed with the plasmid expressing the SRD1::GFP fusion protein (FIG. 5), indicating that SRD1 is a nuclear-localized protein. This result suggests that SRD1, like many of the other MADS-box genes identified to date, is most probably a transcription factor.

EXAMPLE 4

Localization of SRD1 Transcripts in the Storage Root

In situ hybridization was used to determine the localization of SRD1 mRNA accumulation in developing storage roots. Storage roots (0.5 cm in diameter) were cut transversely and fixed with FAA comprising 50% ethanol, 5% acetic acid, and 3.7% formaldehyde at 4° C. for 10 d. The samples were then dehydrated stepwise for 30 min in increasing concentrations of ethanol (50, 60, 70, 80, 90, 95, and 100%), embedded in paraffin (Sigma) for 5 d, and cut into 10 μm thick slices on coated slides. The sections were treated with xylene followed by hydration, proteinase K treatment, acetylation, and dehydration. The full-length SRD1 sequence was used as a probe. Digoxigenin (DIG)-labelled sense and antisense SRD1 probes were synthesized with T3 and T7 RNA polymerases using a DIG RNA labeling kit (Roche Diagnostics) according to the manufacturer's instructions. Hybridization and detection were performed following the protocol described by Shin et al. (2006, Planta 224, 32-41). Accumulation of SRD1 mRNA was analyzed under bright field microscopy (BX51; Olympus) equipped with a CCD camera (DP70; Olympus).

Figure 6:
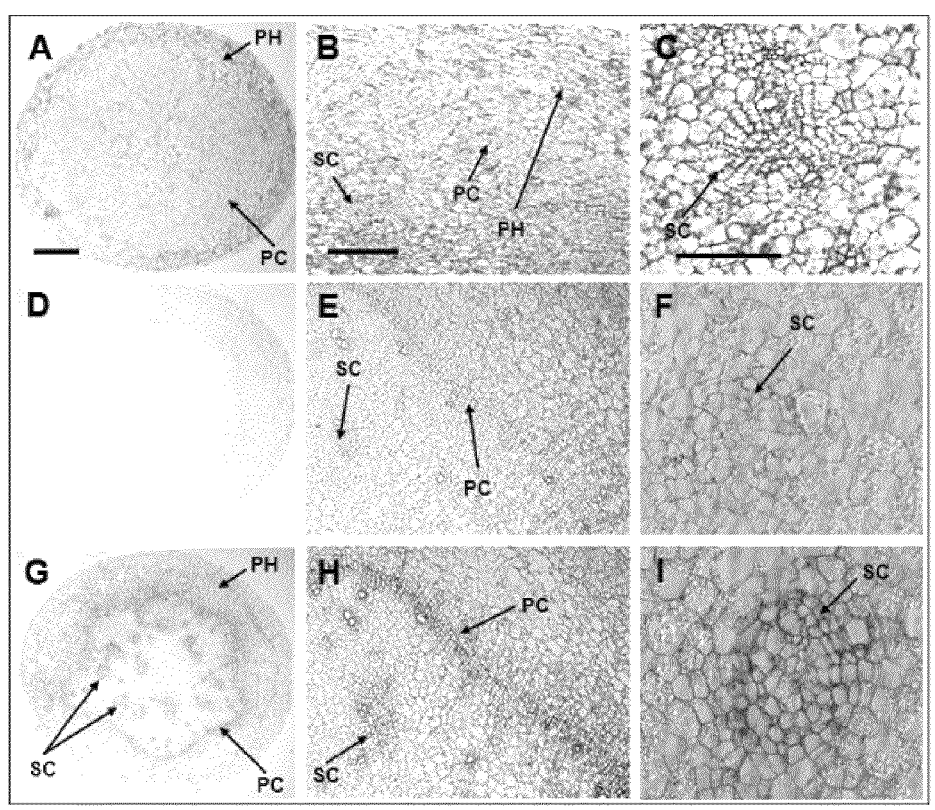
FIG. 6 shows localization of SRD1 transcripts in storage root of sweetpotato. (A-C) Cross-section of a young storage root, (D-F) cross-section hybridized with the sense riboprobe, (G-I) cross-section hybridized with the antisense riboprobe. PC, primary cambium; SC, secondary cambium; PH, primary phloem.

The presence of a violet stain, indicating a positive hybridization signal, i.e. the SRD1 transcript, was mainly observed in the actively dividing cells, including the vascular and cambium cells of the storage root. Among them, accumulation of the SRD1 transcript was remarkably detected in the primary cambium (PC), primary phloem cells (PH) and secondary cambium (SC) (FIG. 6). No hybridization signal was detected in the storage parenchyma cells and xylem vessels. This result indicates that SRD1 plays a role in the onset of thickening growth in the storage roots of sweetpotato, because cells divide most actively in the primary cambium and secondary cambium during the initial thickening growth of storage roots.

EXAMPLE 5

Analysis of Transcriptional Regulation of SRD1 in Response to Exogenous IAA

To determine the transcriptional regulation of SRD1, SRD1-specific primers [5'-AGAGGAGAAATGGGT-TGTTTA-3'(SEQ ID NO.: 10) and 5'-GTGCACGAAACTC-CCCTT-3'(SEQ ID NO.: 11)] were designed to contain nucleotide 180 (the nucleotide showing an SNP between SRD1 and IbMADS1) and the 3 bp deletion region in SRD1 at the 3' end of the forward primer and at the 3' end of the reverse primer, respectively (FIG. 1). These primers selectively amplified the SRD1 sequence but did not amplify the IbMADS1 sequence, when PCR amplification was performed using these primers at the annealing temperature 58° C.

The roots of sweetpotato were treated with IAA according to the following method. Sweetpotato plantlets bearing a single leaf and petiole (single-leaf plantlets) were collected from sweetpotato plants and incubated in flasks containing distilled water for 3 weeks. After fibrous roots had developed from the distal end of the petiole, the single-leaf plantlets were incubated in various concentrations of IAA (0, 50, 500, 1000, 2000 μM) at 25° C. in the dark for various time periods (0-24 h). After the hormone treatment, total RNA was extracted from the fibrous roots using the RNeasy Plant Mini Kit™ (Qiagen) and used for real-time and semi-quantitative reverse transcription-PCR (RT-PCR).

Total RNA (5 μg) was used for first-strand cDNA synthesis using the SuperScript III first-strand cDNA synthesis kit (Invitrogen). The resulting cDNA solution was then diluted with 30 μl of TE (10 mM TRIS-HCl, pH 8.0, 1 mM EDTA). The primers for real-time RT-PCR were as follows: SRD1 (5'-AGAGGAGAAATGGGTTGTTTA-3'; SEQ ID NO.: 10), 5'-GTGCACGAAACTCCCCTT-3'; SEQ ID NO. 11). Real-time PCR analysis was performed using the LightCycler 480 quantification system (Roche Diagnostics) according to the manufacturer's instructions. Expression levels were normalized with β-tubulin expression amplified with 5'-CAACTAC-CAGCCACCAACTGT-3' (SEQ ID NO.: 12) and 5'-CA-GATCCTCACGAGCTTCAC-3' (SEQ ID NO.: 13) primers. PCR were performed starting with pre-denaturation at 95° C. for 10 min before 45 cycles of denaturation at 95° C. for 10 sec, annealing at 58° C. for 10 sec and extension at 72° C. for 20 sec. Following the amplification phase, a melting curve analysis was conducted from 65° C. to 97° C. The second derivative maximum method in the LightCycler 480 quantification software (Roche Diagnostics) was used to evaluate the data.

Figure 7:
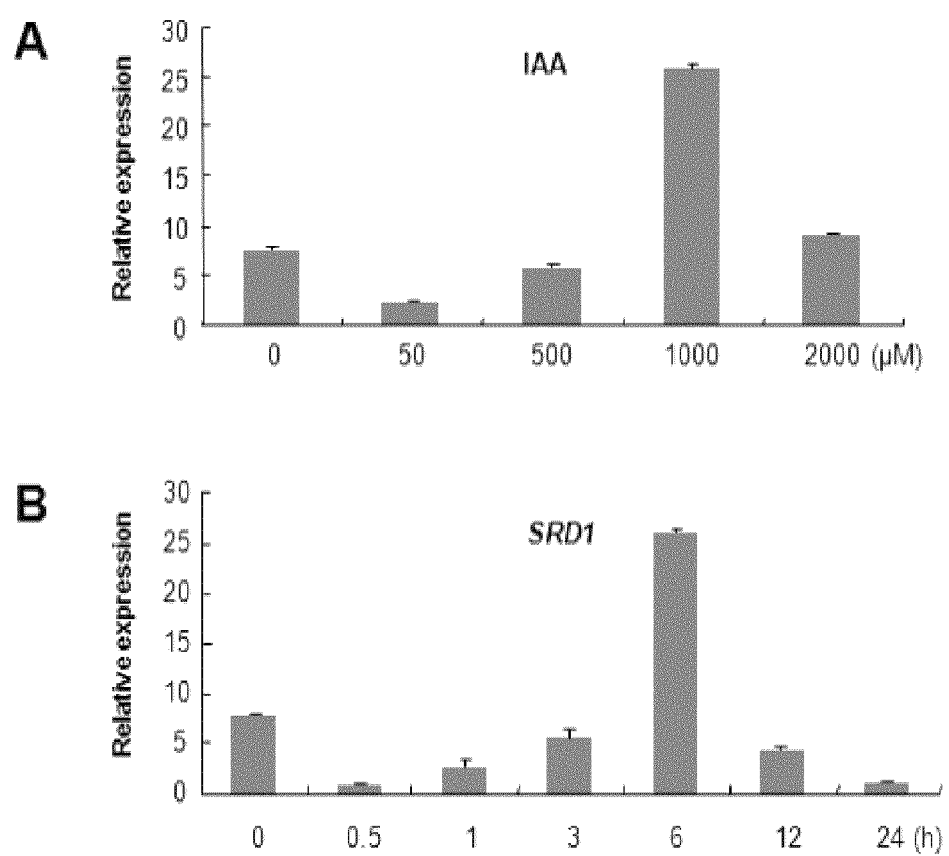
FIG. 7 shows effect of auxin on the expression of SRD1. (A) Transcript levels of SRD1 in response to treatment with various concentrations of exogenous IAA (Indole-3-acetic acid). (B) Time course of the expression of SRD1 in response to IAA (500 µM) for various time periods (0-24 h).

The SRD1 mRNA levels were regulated in response to exogenously applied IAA. The transcript level of SRD1 decreased at 50 μM and 500 μM IAA, but increased sharply at 1000 μM IAA (FIG. 7A). At 2000 μM IAA, however, it had decreased to almost the same level as that observed at 0 μM IAA. A time course study of SRD1 expression (0, 0.5, 1, 3, 6, 12, and 24 h) in fibrous roots cultured in 500 μM IAA revealed that the transcript level of SRD1 increased sharply at 6 h after treatment but that this transcript level of SRD1 decreased compared with the control at 0.5, 1, 3, 12, and 24 h after treatment (FIG. 7B). Taken together, these results suggest that the transcript level of SRD1 is finely regulated in response to IAA concentration, with increases in the SRD1 transcript level occurring only at specific concentrations of IAA and at specific times after IAA treatment.

EXAMPLE 6

Transcript Level of SRD1 During Early-Stage Storage Root Development

Based on the transcriptional regulation of SRD1 in response to IAA concentration, the transcript level of SRD1 in response to the endogenous IAA concentration was analyzed at various developmental stages of sweetpotato storage roots.

Sweetpotato roots (1.0, 1.5, 3.0, 5.0 mm in diameter) were harvested to measure the concentration of IAA. The concentration of IAA was determined as described by Boonplod (2005, PhD thesis, University of Hohenheim, Stuttgart, Germany) with some modifications. Briefly, the lyophilized sample of fresh sweetpotato storage roots (10 g) was homogenized in 80% cold methanol (50 ml) and then kept in darkness at 4° C. overnight. The methanol extracts were concentrated completely by vacuum evaporation, dissolved in 4 ml of 0.01 M ammonium acetate (pH 9.0), and then centrifuged at 20000 rpm for 20 min. The supernatant was loaded on a column filled with 10 mL of polyvinylpyrrolidone (PVP; Sigma) and 4 mL of DEAE-Sephadex A-25 (Sigma). Anionic compounds containing free IAA bound to the column were eluted by 0.1 M acetic acid and further purified by loading on the $C_{18}$Sep-PaK cartridge (Sigma). The IAA was eluted from the cartridge with 4 ml of 40% methanol in 0.1 M acetic acid. After evaporation of the methanol, the samples in duplicate were subjected to quantitative analysis for auxin using the Phytodetek™ -IAA immunoassay detection kit (Agdia Inc., ID, USA) according to the manufacturer's instructions.

Figure 8:
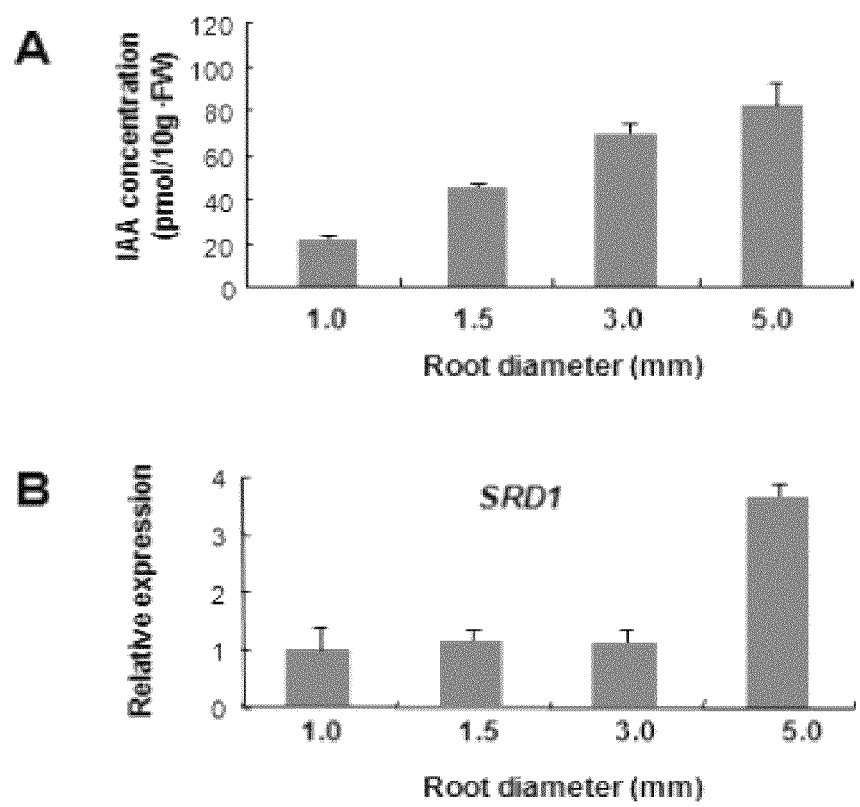
FIG. 8 shows an increase of SRD1 transcript levels in proportion to the rise in endogenous IAA levels during early-stage storage root development. (A) Endogenous IAA levels in various-sized (1.0-5.0 mm in diameter) roots. (B) Transcript levels of SRD1 in the roots with designated maximum diameters.

The endogenous IAA content increased gradually with increasing root diameter up to 5 mm (FIG. 8A). Ultimately, the IAA content in the storage roots (diameter 5 mm) was 4-fold higher than that in unpigmented fibrous roots (diameter 1 mm), indicating that there was a large increase in the endogenous IAA level during the early stage of storage root development.

The effect of this increased endogenous IAA content on the transcript levels of SRD1 was also determined (FIG. 8B). Total RNA was extracted from sweetpotato roots (1, 1.5, 3, and 5 mm in diameter) according to the method described by You et al. (2003, FEBS Letters 536, 101-105) and used in RT-PCR. PCR was performed using the method of Example 5.

Real-time PCR analysis revealed that the transcript level of SRD1 was elevated in response to increasing IAA content which increases in proportion to the thickening of sweetpotato storage roots. The SRD1 transcript level was shown to increase by 3.5 folds in the 5-mm-diameter storage roots in response to increasing IAA content. The transcript level of SRD1, however, remained unchanged in the pigmented fibrous root (diameter 1.5 mm) and thick root (diameter 3.0 mm), although the endogenous IAA level gradually increased. This finding indicates that a certain level of IAA is required for the up-regulation of SRD1 transcription and that this level is at a minimum critical concentration in the 5-mm-diameter storage root.

It has been reported that the presence of anomalous secondary cambium is a morphological characteristic of the storage root, and secondary meristem has been shown to be activated in the 5-mm-diameter roots (Wilson and Lowe, 1973, Annals in Botany 37, 633-643; Nakatani and Komeichi, 1991, Japanese Journal of Crop Science 60, 91-100). Consequently, these results demonstrate that SRD1 plays a role in the development of the secondary cambium controlled by IAA.

EXAMPLE 7

Construction of Binary Vector and Transformation of Sweetpotato

To directly investigate the biological function of SRD1 in the sweetpotato, a binary vector for over-expression was prepared. The full-size SRD1 cDNA amplified with T3 and T7 primers was cloned into the BamHI and KpnI sites of the pMBP1 binary vector. The resulting construct was introduced into *Agrobacterium* strain GV3101 and used for sweetpotato transformation by an *A. tumefaciens*-mediated method. Embryogenic calli were induced from *I. batatas* (L.) Lam. cv. 'Yulmi' shoot apical meristems cultured on MS medium (Murashige 1 and Skoog, 1962, Physiologia Plantarum 15, 473-497) supplemented with 1 mg/L 2,4-dichlorophenoxy-acetic acid (2,4-D), 3% sucrose, and 0.4% gelrite (MS1D), kept at 25° C. in the dark, and proliferated by subculturing at 4 week intervals on the same fresh medium. After co-culture of embryogenic calli with *A. tumefaciens*, embryogenic calli were kept on MS1D medium containing 100 mg/L kanamycin and 400 mg/L claforan (selection medium) at 25° C. in the dark and subcultured under the same conditions every 3 weeks for 4-5 months. Somatic embryos were induced by transferring kanamycin-resistant calli to hormone-free MS medium containing 100 mg/L kanamycin. Regenerated plants were cultured on the same medium and maintained at 25° C. under a 16/8 h (light/dark) cycle.

EXAMPLE 8

Identification and Expression Analysis of Transgenic Sweetpotato Plants

Figure 9:
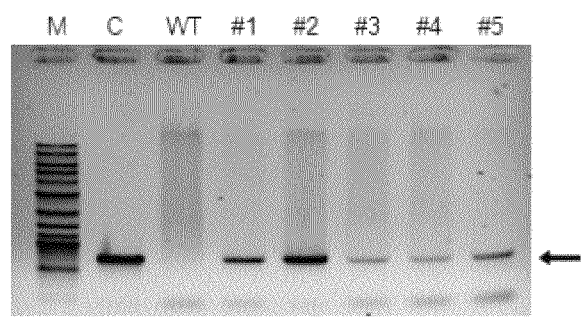
FIG. 9 shows verification of the insertion of the SRD1 gene in the SRD1-ox sweetpotato plants in which sweetpotato SRD1 cDNA of the present subject matter is inserted. M, size marker; C, positive control (pMBP1 containing full-length SRD1 cDNA); WT, wild-type.

Functional transformants were identified by PCR analysis of genomic DNA from leaves of SRD1-ox sweetpotato plants cultured in vitro, using the SRD1-specific primer (5'-CTT-TAATAAGTTTCAGGCATATGG-3': SEQ ID NO.: 14) and NOS terminator primer (5'-CGCGCGCGATAATTTATCC-3': SEQ ID NO.: 15) (FIG. 9).

Figure 10:
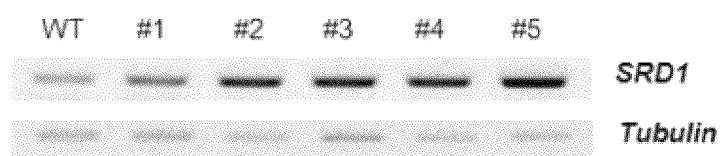
FIG. 10 shows transcript levels of SRD1 gene in the SRD1-ox sweetpotato plants in which sweetpotato SRD1 cDNA of the present subject matter has been inserted.

To measure SRD1 expression level in the transgenic plants, total RNA was isolated from fibrous roots of the transformed sweetpotato using RNeasy Plant Mini Kit (Qiagen). First-strand cDNA was synthesized using SuperScript™ III first-strand synthesis mix (Invitrogen, USA) for RT-PCR analysis. RT-PCR was performed using SRD1-specific primers (5'-AGAGGAGAAATGGGTTGTTTA-3' (SEQ ID NO.: 10); 5'-GTGCACGAAACTCCCCTT-3' (SEQ ID NO.: 11)), starting from pre-denaturation at 95° C. for 5 min, with 30 cycles of denaturation at 94° C. for 30 sec, annealing at 58° C. for 30 sec and extension at 72° C. for 30 sec, followed by a final 5-min extension at 72° C. The sweetpotato β-tubulin gene was used as an equal loading internal control. SRD1 transcript accumulation in the fibrous roots of the SRD1-ox transgenic lines was moderately elevated in line 1 and strongly elevated in lines 2, 3, 4, and 5 (FIG. 10). Lines 1 and 3 were selected for further phenotypic analysis.

EXAMPLE 9

Growth Analysis of Transgenic Sweetpotato Roots

Figure 11:
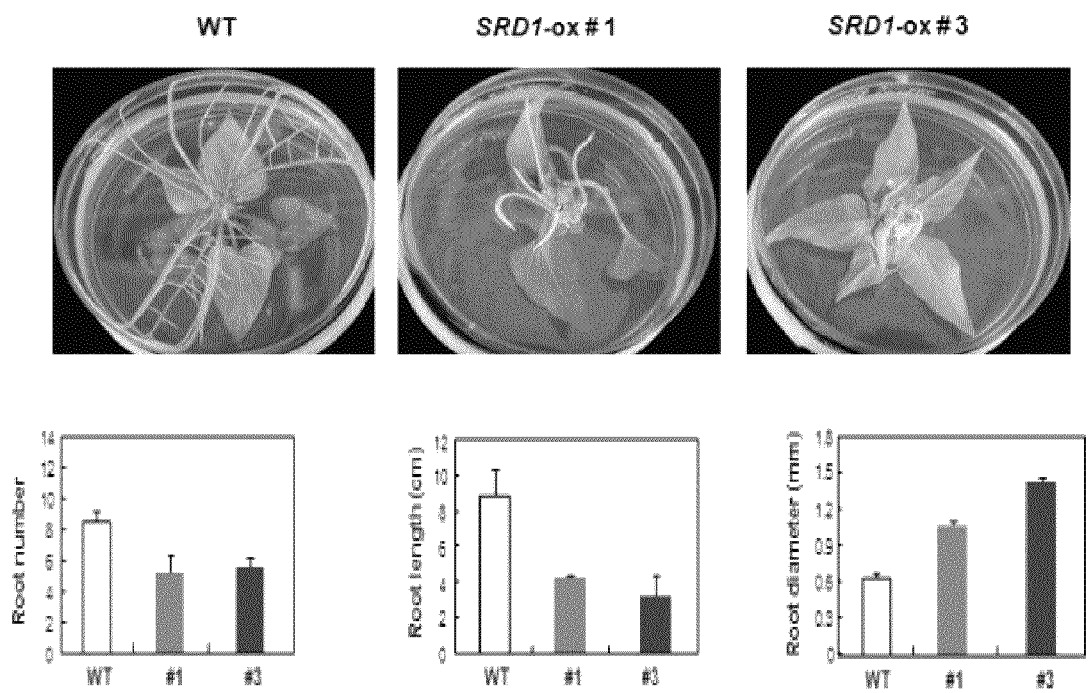
FIG. 11 shows a comparison of the growth of roots in the SRD1-ox sweetpotato plants in which sweetpotato SRD1 cDNA of the present subject matter has been inserted, with growth of wild type roots.

Growth pattern of roots were compared between the SRD1-ox sweetpotato plants and the wild type. Cuttings of SRD1-ox sweetpotato plants bearing the apical meristem and 2-3 leaves were grown on MS medium at 25° C. for 14 d under long-day conditions. Root morphogenesis occurred at 2 weeks after planting. SRD1-ox 1 and 3 plants produced thicker and longer fibrous roots compared to the wild type. The number of fibrous roots decreased in SRD1-ox sweetpotato (FIG. 11 and Table 1).

Transverse sections of the maturation zone (taken at 1.0 cm intervals beginning from the root tip) were prepared from the thickest fibrous root of the wild-type and SRD1-ox plants in order to study the phenotype at the cellular level in more detail. Samples were fixed with 2% (w/v) paraformaldehyde and 2% (v/v) glutaraldehyde in 0.1 M sodium phosphate buffer, pH 7.0, at 4° C. for 10 d. After fixation, the tissues were washed twice in 0.1 M sodium phosphate buffer for 5 min, dehydrated stepwise for 30 min in a graded series of ethanol (50, 60, 70, 80, 90, 95, and 100%), embedded in acrylic resin (LR White; London Resin Company) for 5 d, and cut into 1.0 μm thick sections. The sections were stained with 1% safranin O and observed under light microscopy (BX51; Olympus).

Cell proliferation was significantly enhanced in the SRD1-ox plants, resulting in an increase in the number of cells in the primary cambium (PC) and the metaxylem (MX) compared with the wild type (FIG. 12; Table 2). The extent of the increase in cell proliferation was more severe in SRD1-ox 3 than in 1, suggesting that the increase in cell proliferation was attributable to the increased levels of SRD1 mRNA accumulation. In particular, in mutant 3 plants showing strongly increased expression of SRD1, the circular secondary cambium as well as the primary cambium had differentiated around discrete protoxylem (PXY). It has been reported that such cell proliferation (cell division of the metaxylem cells and the primary cambium cells) appears in early phase transition from the fibrous root to the storage root, and that the secondary cambium is a morphological marker in the storage roots of sweetpotato. Taken together, these results indicate that SRD1 plays a role in the initial thickening growth of storage roots by activating the proliferation of the cambium and metaxylem cells. Table 1 shows the effect of SRD1 over-expression on the thickening growth of fibrous root. Table 2 shows the effect of SRD1 overexpression on the proliferation activities of cells in the fibrous root.

TABLE 1

| Root area | WT[a] | 1 | | 3 | |
|---|---|---|---|---|---|
| | D[b](μm) | D[b](μm) | Rate[c] | D[b](μm) | Rate[c] |
| Cortex + stele[d] | 640 ± 35 | 1064 ± 55 | 1.66 ± 0.02 | 1400 ± 37 | 2.12 ± 0.06 |
| Cortex[e] | 480 ± 27 | 784 ± 48 | 1.64 ± 0.01 | 1024 ± 42 | 2.10 ± 0.03 |
| Stele[f] | 160 ± 13 | 280 ± 11 | 1.68 ± 0.07 | 376 ± 22 | 2.30 ± 0.05 |

[a]Wild type.
[b]Diameter measured with transverse sections of fibrous roots.
[c]Expansion rate relative to the wild type.
[d]Determined by measuring the largest diameter on the circle enclosed by epidermal cells.
[e]Calculated by subtracting the diameter of the stele from the diameter of the cortex and stele.
[f]Determined by measuring the largest diameter on the circle enclosed by endodermis cells.

TABLE 2

| Cell type | WT[a] No. of cells[b] | 1 No. of cells[b] | 1 Rate[c] | 3 No. of cells[b] | 3 Rate[c] |
|---|---|---|---|---|---|
| Cortex | 232 ± 18 | 503 ± 39 | 2.17 ± 0.00 | 570 ± 15 | 2.46 ± 0.12 |
| Stele[d] | 140 ± 3 | 432 ± 2 | 3.08 ± 0.05 | 538 ± 11 | 3.84 ± 0.01 |
| Metaxylem[e] | 26 ± 3 | 108 ± 13 | 4.15 ± 0.32 | 127 ± 5 | 4.88 ± 0.33 |
| Cambium | 44 ± 6 | 100 ± 7 | 2.27 ± 0.13 | 161 ± 35 | 3.66 ± 0.26 |

[a]Wild type.
[b]Counted on transverse sections of fibrous roots.
[c]Proliferation rate relative to the wild type.
[d]Number of all cells inside the endodermis cells.
[e]Numbers of metaxylem cells including mature and immature metaxylem cells.

EXAMPLE 10

Analysis of Storage Root Production in SRD1-ox Sweetpotato Plants

Figure 13:
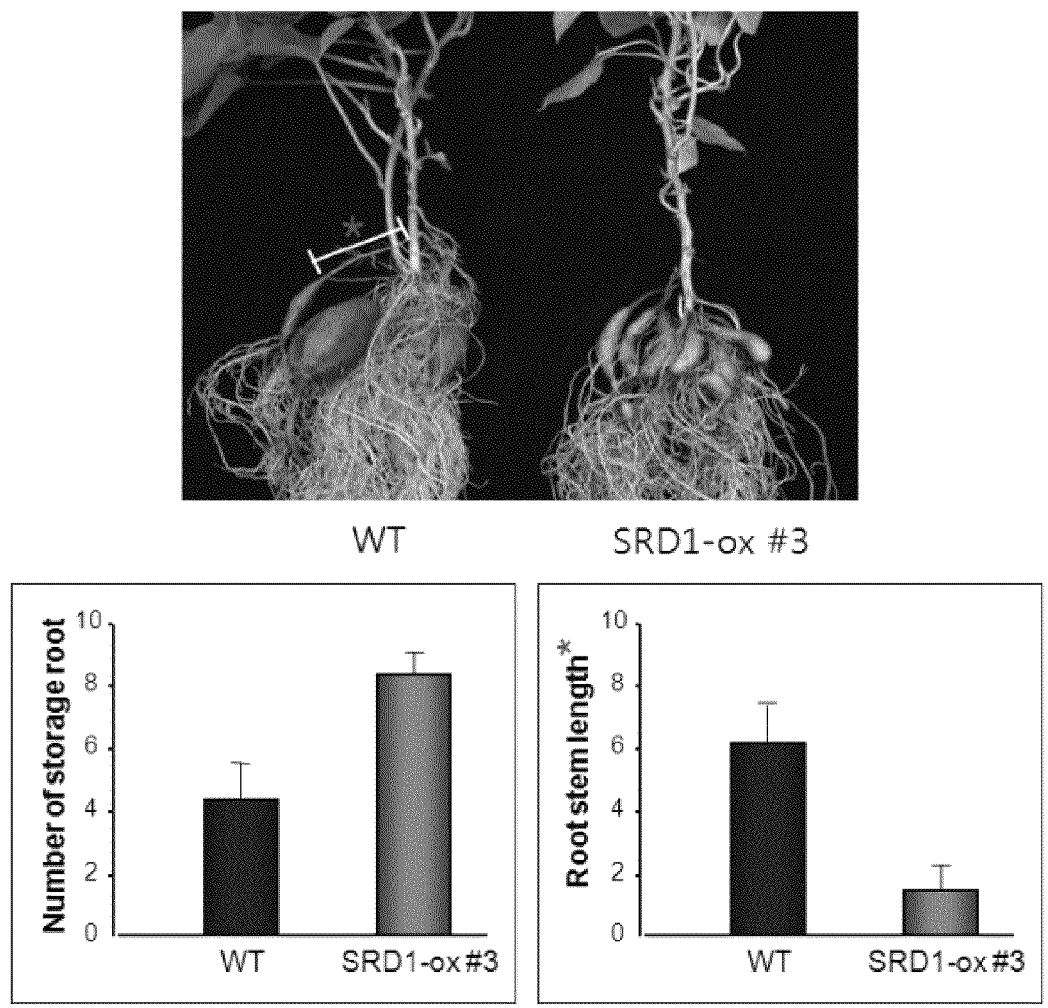
FIG. 13 shows a comparison of the productivity of storage roots in the SRD1-ox sweetpotato plants in which sweetpotato SRD1 cDNA of the present subject matter has been inserted, with the productivity of storage roots in wild type.

To examine the storage root production in SRD1-ox sweetpotato plants, regenerated plantlets were transplanted into pots and grown in the greenhouse for 4 months. The storage root production was increased in SRD1-ox sweetpotato plants, being about 2-fold higher than that of the wild type (FIG. 13).

The sizes of the storage roots from SRD1-ox sweetpotato plants were also homogeneous, whereas those of the wild type were diverse. Furthermore, the position from which storage roots developed in SRD1-ox sweetpotato plants were different from those in the wild type. The length of the root stem defined as the part between the topmost position of fibrous root and the proximal end of storage root in sweetpotato (* in FIG. 13) decreased significantly in SRD1-ox #3, being about ⅕ of the wild type.

The increased number of storage roots in SRD1-ox sweetpotato plants indicates that the development of storage roots was stimulated by the over-expression of SRD1. The decrease in the length of root stems in the transgenic sweetpotato plants indicates that the development of storage roots was initiated earlier in the SRD1-ox sweetpotato plants than in the wild type. Consequently, transgenic plants with high-numbered storage roots were produced by over-expressing SRD1 which is involved in thickening growth of the storage root.

Therefore, SRD1 cDNA according to the present subject matter is very useful in the generation of transgenic plants that have enhancements in the development of storage roots, particularly in the generation of transgenic root crops with high-numbered storage roots.

EXAMPLE 11

Transformation of *Arabidopsis* and Analysis of Expression Pattern

SRD1-ox *Arabidopsis* was prepared to identify whether the functional role of SRD1 is the same as that of IbMADS1 because of high homogeneity between them.

More particularly, the vector constructed in Example 5 was introduced into *Agrobacterium tumefaciens* C58C1 using a freeze-thaw method (An, G. 1987, Methods in Enzymology). The *Agrobacterium* carrying the gene of interest in the vector was cultured at 28° C. for 2 days with agitation and then brought into contact with stigma of *Arabidopsis* (*Arabidopsis thaliana* cv. Columbia) just before flowering so as to transform the plant on the basis of the floral dip method (Clough and Bent, 1998, The Plant Journal).

Seeds were harvested from the *Arabidopsis* transformants and plated on tissue culture MS plates with 30 mg/L Kanamycin. Selected tranformants (T1) that showed a segregation ratio of 3:1 for kanamycin resistance due to the introduction of a single copy of the SRD1 cDNA were transplanted into soil and grew, and homozygous seeds were harvested. T3 homozygous seeds were transplanted into soil to investigate the growth of transgenic *Arabidopsis* compared with that of the wild type.

Figure 14:
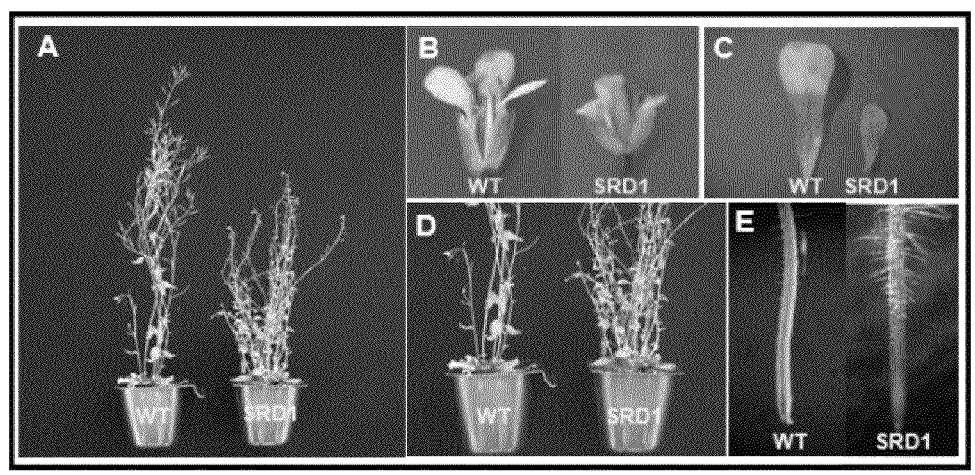
FIG. 14 shows a comparison of the growth and development of the SRD1-ox *Arabidopsis* plants in which sweetpotato SRD1 cDNA of the present subject matter has been inserted, with the growth and development of wild type plants.

The number of inflorescence stems of transgenic plants was increased significantly, resulting in a long-lasting flowering time. The height of the inflorescence stem was shorter and the size of the flower was smaller in transgenic plants than that in the wild type (FIG. 14). Development of the fibrous roots of in transgenic plants had enhanced relative to the wild type, resulting in an increased number and length of the fibrous roots.

Meanwhile, Ku et al. reported that no phenotypic difference was observed in the flower tissues and flowering time between IbMADS1-ox potato plants and wild type. But, the phenotype of SRD-ox *Arabidopsis* was different from that of IbMADS1-ox *Arabidopsis* plants. These results indicate that SRD1 is a distinct gene from IbMADS1 in terms of functional role. As such, SRD1 is the first sweetpotato gene whose role in storage root development has been directly characterized in a transgenic sweetpotato.

Industrial Applicability

As described hitherto, the present subject matter provides an SRD1 cDNA that is involved in the increased number of storage roots and in inducing the earlier development of storage roots by stimulating storage root development. Therefore, the present subject matter is useful in the generation of transgenic root crops with high-numbered storage roots or early-maturing storage root plants, such as high value-added storage root plants (ginseng and sweetpotato, etc.).

Although the preferred embodiments of the present subject matter have been disclosed for illustrative purposes, those skilled in the art will appreciate that various modifications, additions and substitutions are possible, without departing from the scope and spirit of the invention as disclosed in the accompanying claims.

What is claimed is:

1. A binary vector for transforming plants, comprising an isolated DNA molecule comprising the nucleic acid sequence SEQ ID NO.: 1.

2. A microorganism, comprising the binary vector of claim 1.

3. A transgenic plant, comprising the binary vector of claim 1.

4. A binary vector for transforming plants, comprising an isolated DNA molecule comprising the nucleotide sequence of SEQ ID NO. 3.

5. A microorganism, comprising the binary vector of claim 4.

6. A transgenic plant, comprising the binary vector of claim 4.

7. An isolated polypeptide, translated from an isolated DNA molecule comprising the nucleic acid sequence of SEQ ID NO.: 1.

8. A method for increasing the number of plant storage roots, comprising introducing the binary vector according to claim 1 into plants and expressing the DNA molecule within the binary vector, thereby increasing the number of plant storage roots.

9. A method for stimulating thickening growth of plant storage roots, comprising introducing the binary vector according to claim 1 into plants and expressing the DNA molecule within the binary vector, thereby stimulating thickening growth of plant storage roots.

10. A method for producing homogenous-sized storage roots of plants, comprising introducing the binary vector according to claim 1 into plants and expressing the DNA molecule within the binary vector, thereby producing homogenous-sized storage roots of plants.

11. A method for increasing the number of plant storage roots, comprising introducing the binary vector according to claim 4 into plants and expressing the ORF within the binary vector, thereby increasing the number of plant storage roots.

12. A method for stimulating the thickening growth of plant storage roots, comprising introducing the binary vector according to claim 4 into plants and expressing the ORF within the binary vector, thereby stimulating thickening growth of plant storage roots.

13. A method for producing homogenous-sized storage roots of a plant, comprising introducing the binary vector according to claim 4 into the plant and expressing the ORF within the binary vector, thereby producing homogenous-sized storage roots of a plant.

14. A method for regulating the development of a plant storage root of a transgenic plant comprising an isolated DNA molecule comprising the nucleic acid sequence of SEQ ID NO.: 1, comprising treating the transgenic plant with an auxin, thereby inducing expression of the isolated DNA molecule which regulates the development of the plant storage root.

* * * * *

SEQUENCE LISTING

<160> NUMBER OF SEQ ID NOS: 17

<210> SEQ ID NO 1
<211> LENGTH: 1002
<212> TYPE: DNA
<213> ORGANISM: Ipomoea batatas cv. Jinhongmi

<400> SEQUENCE: 1

```
ctagcgtctt caacaattct accctactat catccccccaa gacttccccg accagctgca      60
gaaaacccca tcccagaaat agggaggaga aggatgggga ggggcaaggt tgaaattagg     120
aggatcgaaa agtcgaccaa caggcgagtc accttctgga agaggagaaa tgggttgttt     180
aagaaggcta tggagatggg gattctgtgc gatgctgaag tgggattgat gatcttctcc     240
agcacaggga agctccatga attcgcaaca actagcatca gatccgtaat tgaacgctac     300
aacaagacac aaggtgacag ccttcaatcc cctctggacc caacattaga actcaagttt     360
tggcaaatag aagtagcaat tctgaggcaa caattacaca acatgcaaga agatcatcgg     420
aaagtaatgg gagaagtcta tgggctgagt gttaaagacc tgcagaatct gaaaaccaa      480
ctggaaatga gtttgagcgg catcagaatg aagaaggaac aaatactaat tgaacagatt     540
caagaactaa cccacaaggg gagtttcgtg caccaggaaa actttgaact ctttaataag     600
tttcaggcat atggcacaag tgacccaaat gcagtgaatg gggacaccat ttctccatat     660
gacttcacca ttagtgaaga tcccaaggc cacatacatt tccagcttcc tcaaaacttc      720
agcgatctag ccagagcatt atattagact caacgtaaat gatgcagctg ctgatgaata     780
aaattcaaga gaattattc cgagtgatgg tgggccgtgg aaactccaag tatgggatgg      840
tggactatcc tctattaaaa tatcaaatgt acctgagaat ataatcttct ccttgtggtc     900
ttatggcagt gtttttgaat tgtgggattc gtgtgttttg agttgtatgt aggttttaa      960
attggtgttt gatgttaaat aaactgatcg agcttaactg tt                       1002
```

<210> SEQ ID NO 2
<211> LENGTH: 217
<212> TYPE: PRT
<213> ORGANISM: Ipomoea batatas cv. Jinhongmi

<400> SEQUENCE: 2

Met Gly Arg Gly Lys Val Glu Ile Arg Arg Ile Glu Lys Ser Thr Asn
  1               5                  10                  15

Arg Arg Val Thr Phe Trp Lys Arg Asn Gly Leu Phe Lys Lys Ala
             20                  25                  30

Met Glu Met Gly Ile Leu Cys Asp Ala Glu Val Gly Leu Met Ile Phe
         35                  40                  45

Ser Ser Thr Gly Lys Leu His Glu Phe Ala Thr Thr Ser Ile Arg Ser
     50                  55                  60

Val Ile Glu Arg Tyr Asn Lys Thr Gln Gly Asp Ser Leu Gln Ser Pro
 65                  70                  75                  80

Leu Asp Pro Thr Leu Glu Leu Lys Phe Trp Gln Ile Glu Val Ala Ile
                 85                  90                  95

Leu Arg Gln Gln Leu His Asn Met Gln Glu Asp His Arg Lys Val Met
            100                 105                 110

Gly Glu Val Tyr Gly Leu Ser Val Lys Asp Leu Gln Asn Leu Glu Asn
        115                 120                 125

Gln Leu Glu Met Ser Leu Ser Gly Ile Arg Met Lys Lys Glu Gln Ile
    130                 135                 140

```
Leu Ile Glu Gln Ile Gln Glu Leu Thr His Lys Gly Ser Phe Val His
145                 150                 155                 160

Gln Glu Asn Phe Glu Leu Phe Asn Lys Phe Gln Ala Tyr Gly Thr Ser
                165                 170                 175

Asp Pro Asn Ala Val Asn Gly Asp Thr Ile Ser Pro Tyr Asp Phe Thr
            180                 185                 190

Ile Ser Glu Glu Ser Gln Gly His Ile His Phe Gln Leu Pro Gln Asn
        195                 200                 205

Phe Ser Asp Leu Ala Arg Ala Leu Tyr
    210                 215
```

<210> SEQ ID NO 3
<211> LENGTH: 654
<212> TYPE: DNA
<213> ORGANISM: Ipomoea batatas cv. Jinhongmi

<400> SEQUENCE: 3

```
atggggaggg gcaaggttga aattaggagg atcgaaaagt cgaccaacag gcgagtcacc      60
ttctggaaga ggagaaatgg gttgtttaag aaggctatgg agatggggat tctgtgcgat     120
gctgaagtgg gattgatgat cttctccagc acagggaagc tccatgaatt cgcaacaact     180
agcatcagat ccgtaattga cgctacaac aagacacaag gtgacagcct tcaatcccct      240
ctggacccaa cattagaact caagttttgg caaatagaag tagcaattct gaggcaacaa     300
ttacacaaca tgcaagaaga tcatcggaaa gtaatgggag aagtctatgg ctgagtgtt      360
aaagacctgc agaatcttga aaccaactg gaaatgagtt tgagcggcat cagaatgaag      420
aaggaacaaa tactaattga acagattcaa gaactaaccc acaaggggag tttcgtgcac     480
caggaaaact ttgaactctt taataagttt caggcatatg gcacaagtga cccaaatgca     540
gtgaatgggg acaccatttc tccatatgac ttcaccatta gtgaagaatc ccaaggccac     600
atacatttcc agcttcctca aaacttcagc gatctagcca gagcattata ttag           654
```

<210> SEQ ID NO 4
<211> LENGTH: 1022
<212> TYPE: DNA
<213> ORGANISM: Ipomoea batatas

<400> SEQUENCE: 4

```
gatttccatg ttggtgtgaa caaccaccta aacctagcgt cttcaacaat tctaccctac      60
tatcatcccc caagacttcc ccgaccagct gcagaaaacc ccatcccaga aatagggagg     120
agaaggatgg ggaggggcaa ggttgaaatt aggaggatcg aaaagtcgac caacaggcga     180
gtcaccttct ggaagaggag aaatgggttg ttgaagaagg ctatggagat ggggattctg     240
tgcgatgctg aagtgggatt gatgatcttc tccagcacag gaagctcca tgaattcgca      300
acaactagca tcagatccgt aattgaacgc tacaacaaga cacaaggtga cagccttcaa     360
tccccctctgg acccaacatt agaactcaag ttttggcaaa tagaagtagc aattctgagg    420
caacaattac acaacatgca agaagatcat cggaaagtaa tgggagaagt ctatggctg     480
agtgttaaag acctgcagaa tcttgaaaac caactggaaa tgagtttgag cggcatcaga    540
atgaagaagg aacaaatact aattgaacag attcaagaac taacccacaa gcaggggagt    600
ttcgtgcacc aggaaaactt tgaactcttt aataagtttc aggcatatgg cacaagtgac    660
ccaaatgcag tgaatgggga caccatttct ccatatgact tcaccattag tgaagaatcc    720
caaggccaca tacatttcca gcttcctcaa aacttcagcg atctagccag agcattatat    780
```

```
tagactcaac gtaaatgatg cagctgctga tgaataaaat tcaagagaaa ttattccgag    840
tgatggtggg ccgtggaaac tccaagtatg ggatggtgga ctatcctcta ttaaaatatc    900
aaatgtacct gagaatataa tcttctcctt gtggtcttat ggcagtgttt ttgaattgtg    960
ggattcgtgt gttttgagtt gtatgtaggt ttttaaattg gtgtttgatg ttaaataaac   1020
tg                                                                  1022
```

```
<210> SEQ ID NO 5
<211> LENGTH: 218
<212> TYPE: PRT
<213> ORGANISM: Ipomoea batatas

<400> SEQUENCE: 5
```

Met Gly Arg Gly Lys Val Glu Ile Arg Arg Ile Glu Lys Ser Thr Asn
 1               5                  10                  15

Arg Arg Val Thr Phe Trp Lys Arg Arg Asn Gly Leu Leu Lys Lys Ala
             20                  25                  30

Met Glu Met Gly Ile Leu Cys Asp Ala Glu Val Gly Leu Met Ile Phe
         35                  40                  45

Ser Ser Thr Gly Lys Leu His Glu Phe Ala Thr Thr Ser Ile Arg Ser
     50                  55                  60

Val Ile Glu Arg Tyr Asn Lys Thr Gln Gly Asp Ser Leu Gln Ser Pro
 65                  70                  75                  80

Leu Asp Pro Thr Leu Glu Leu Lys Phe Trp Gln Ile Glu Val Ala Ile
                 85                  90                  95

Leu Arg Gln Gln Leu His Asn Met Gln Glu Asp His Arg Lys Val Met
            100                 105                 110

Gly Glu Val Tyr Gly Leu Ser Val Lys Asp Leu Gln Asn Leu Glu Asn
        115                 120                 125

Gln Leu Glu Met Ser Leu Ser Gly Ile Arg Met Lys Lys Glu Gln Ile
    130                 135                 140

Leu Ile Glu Gln Ile Gln Glu Leu Thr His Lys Gln Gly Ser Phe Val
145                 150                 155                 160

His Gln Glu Asn Phe Glu Leu Phe Asn Lys Phe Gln Ala Tyr Gly Thr
                165                 170                 175

Ser Asp Pro Asn Ala Val Asn Gly Asp Thr Ile Ser Pro Tyr Asp Phe
            180                 185                 190

Thr Ile Ser Glu Glu Ser Gln Gly His Ile His Phe Gln Leu Pro Gln
        195                 200                 205

Asn Phe Ser Asp Leu Ala Arg Ala Leu Tyr
    210                 215

```
<210> SEQ ID NO 6
<211> LENGTH: 20
<212> TYPE: DNA
<213> ORGANISM: Artificial Sequence
<220> FEATURE:
<223> OTHER INFORMATION: PCR PRIMER

<400> SEQUENCE: 6
aattaaccct cactaaaggg                                                 20

<210> SEQ ID NO 7
<211> LENGTH: 22
<212> TYPE: DNA
<213> ORGANISM: Artificial Sequence
<220> FEATURE:
<223> OTHER INFORMATION: PCR PRIMER
```

-continued

```
<400> SEQUENCE: 7
cgggatatca ctcagcataa tg                                             22

<210> SEQ ID NO 8
<211> LENGTH: 24
<212> TYPE: DNA
<213> ORGANISM: Artificial Sequence
<220> FEATURE:
<223> OTHER INFORMATION: PCR PRIMER

<400> SEQUENCE: 8
catcccggga tggggagggg caag                                           24

<210> SEQ ID NO 9
<211> LENGTH: 29
<212> TYPE: DNA
<213> ORGANISM: Artificial Sequence
<220> FEATURE:
<223> OTHER INFORMATION: PCR PRIMER

<400> SEQUENCE: 9
gtgagctcca ctgccataag accacaagg                                      29

<210> SEQ ID NO 10
<211> LENGTH: 21
<212> TYPE: DNA
<213> ORGANISM: Artificial Sequence
<220> FEATURE:
<223> OTHER INFORMATION: PCR PRIMER

<400> SEQUENCE: 10
agaggagaaa tgggttgttt a                                              21

<210> SEQ ID NO 11
<211> LENGTH: 18
<212> TYPE: DNA
<213> ORGANISM: Artificial Sequence
<220> FEATURE:
<223> OTHER INFORMATION: PCR PRIMER

<400> SEQUENCE: 11
gtgcacgaaa ctcccctt                                                  18

<210> SEQ ID NO 12
<211> LENGTH: 21
<212> TYPE: DNA
<213> ORGANISM: Artificial Sequence
<220> FEATURE:
<223> OTHER INFORMATION: PCR PRIMER

<400> SEQUENCE: 12
caactaccag ccaccaactg t                                              21

<210> SEQ ID NO 13
<211> LENGTH: 20
<212> TYPE: DNA
<213> ORGANISM: Artificial Sequence
<220> FEATURE:
<223> OTHER INFORMATION: PCR PRIMER

<400> SEQUENCE: 13
cagatcctca cgagcttcac                                                20

<210> SEQ ID NO 14
<211> LENGTH: 24
<212> TYPE: DNA
```

```
<213> ORGANISM: Artificial Sequence
<220> FEATURE:
<223> OTHER INFORMATION: PCR PRIMER

<400> SEQUENCE: 14
ctttaataag tttcaggcat atgg                                              24

<210> SEQ ID NO 15
<211> LENGTH: 19
<212> TYPE: DNA
<213> ORGANISM: Artificial Sequence
<220> FEATURE:
<223> OTHER INFORMATION: PCR PRIMER

<400> SEQUENCE: 15
cgcgcgcgat aatttatcc                                                    19

<210> SEQ ID NO 16
<211> LENGTH: 17
<212> TYPE: DNA
<213> ORGANISM: Ipomoea batatas cv. Jinhongmi

<400> SEQUENCE: 16
gtttaagaac aagggga                                                      17

<210> SEQ ID NO 17
<211> LENGTH: 20
<212> TYPE: DNA
<213> ORGANISM: Ipomoea batatas cv. Jinhongmi

<400> SEQUENCE: 17
gttgaagaac aagcagggga                                                   20
```